United States Patent [19]

Singh et al.

[11] 4,451,469

[45] May 29, 1984

[54] SELECTED 6-ALKYL-AND 4,6-DIALKYL-2(1H)-PYRIDINONES AS CARDIOTONICS

[75] Inventors: Baldev Singh, East Greenbush; George Y. Lesher, Schodack, both of N.Y.

[73] Assignee: Sterling Drug Inc., New York, N.Y.

[21] Appl. No.: 450,261

[22] Filed: Dec. 16, 1982

[51] Int. Cl.$^3$ .............................................. A61K 31/44
[52] U.S. Cl. ...................................................... 424/263
[58] Field of Search ......................................... 424/263

[56] References Cited

U.S. PATENT DOCUMENTS

| | | | |
|---|---|---|---|
| 3,654,291 | 4/1972 | Witzel et al. | 424/266 |
| 3,754,088 | 8/1973 | Witzel | 424/267 |
| 3,926,935 | 12/1975 | Rogers et al. | 260/96.5 R |
| 4,004,012 | 1/1977 | Lesher et al. | 424/263 |
| 4,038,065 | 7/1977 | Johnson et al. | 71/76 |
| 4,107,315 | 8/1978 | Lesher et al. | 424/263 |
| 4,205,174 | 5/1980 | Michel | 546/249 |
| 4,288,440 | 9/1981 | Youngdale | 424/263 |
| 4,312,875 | 1/1982 | Lesher et al. | 424/263 |

FOREIGN PATENT DOCUMENTS 553097  5/1943  United Kingdom .

OTHER PUBLICATIONS

Bardhan [J. Chem. Soc. 1929, 2223 (2225, 2230) (1939); CA. 24, 617 (1930)].
Basu [J. Indian Chem. Soc., 7, 481 (491) (1930)].
Basu [J. Indian Chem. Soc., 7, 815 (822-3) (1930)].
Baret [J. Indian Chem. Soc. 8, 699 (707) (1931)].
Mariella et al. [J. Am. Chem. Soc. 73, 1368 (1951)].
Kochetkov [C.A. 47, 3309 (1953)].
Mariella [Organic Syntheses, Collective vol. IV, pp. 210–212, Rabjohn (1963)].
Boatman et al. [J. Org. Chem. 30, 3593-7 (1965)].
Sakurai et al. [Bull. Chem. Soc. Japan 40 (7), 1680-4 (1967) (Eng.)].

*Primary Examiner*—Douglas W. Robinson
*Attorney, Agent, or Firm*—Robert K. Bair; B. Woodrow Wyatt; Paul E. Dupont

[57] ABSTRACT

3-Q-4-R'-6-R-2(1H)-pyridinones (I), where Q is hydrogen or cyano, R' is hydrogen, methyl, ethyl or n-propyl, and R is methyl, ethyl or n-propyl, are shown to be useful as cardiotonic agents.

10 Claims, No Drawings

SELECTED 6-ALKYL- AND 4,6-DIALKYL-2(1H)-PYRIDINONES AS CARDIOTONICS

BACKGROUND OF THE INVENTION

1. Field of the Invention

This invention relates to the use of selected 6-alkyl- and 4,6-dialkyl-2(1H)-pyridinones as cardiotonics.

(b) Description of the Prior Art

Bardhan [J. Chem. Soc. 1929, 2223 (2225, 2230) (1930); CA. 24, 617 (1930)] describes, inter alia, the preparation of 3-cyano-6-ethyl-4-methyl-2(1H)-pyridinone (p. 2230, XIV) by reaction of propionylacetone with cyanoacetamide and the conversion of said 3-cyano compound by heating with concentrated hydrochloric acid to the corresponding 6-ethyl-4-methyl-2(1)-pyridinone (pp. 2230, XV).

Basu [J. Indian Chem. Soc. 7, 481 (491) (1930)] describes the preparation of 3-cyano-4,6-dimethyl-2(1H)-pyridinone (p. 491, XVI) by reacting the sodium salt of cyanoacetamide with acetylacetone in anhydrous benzene.

Basu [J. Indian Chem. Soc. 7, 815 (822-3) (1930)] describes the preparation of 3-cyano-4,6-diethyl-2(1H)-pyridinone (p. 822, VI) by reacting dipropionylmethane with cyanoacetamide in ethanol in the presence of diethylamine. In this same paper Basu heated 3-cyano-4,6-diethyl-2(1H)-pyridinone with concentrated hydrochloric acid to produce 4,6-diethyl-2(1H)-pyridinone (pp. 822-3).

Barat [J. Indian Chem. Soc. 8, 699-710 (1931)] describes the preparation of 3-cyano-4,6-dimethyl-2(1H)-pyridinone (p. 707, II, R=Me) by dehydrogenation of 2-keto-3-cyano-4,6-dimethyl-2,3,4,5-tetrahydropyridine with nitrous acid.

Bergel et al [British Pat. No. 553,097, accepted May 7, 1943] shows the reaction of acetylacetone with malononitrile in ethanol in the presence of piperidine to produce 3-cyano-4,6-dimethyl-2(1H)-pyridinone (named as its 5-cyano-2,4-dimethyl-6-hydroxypyridine tautomer).

Mariella et al [J. Am. Chem. Soc. 73, 1368 (1951)] describes the preparation of 3-cyano-6-n-propyl-2(1H)-pyridinone by first reacting methyl n-propyl ketone with sodium and ethyl formate and reacting the resulting sodium salt of hydroxyvinyl n-propyl ketone with cyanoacetamide in the presence of piperidine acetate as catalyst.

Kochetkov [C.A. 47, 3309 (1953)] shows the reaction of $RCOCH_2CH(OC_2H_5)_2$ with cyanoacetamide in the presence of piperidine to produce the 3-cyano-6-R-2(1H)-pyridinones (named as 2-hydroxypyridine tautomers), where R is methyl, n-propyl, isopropyl and n-amyl, and their conversion to the corresponding 6-R-2(1H)-pyridinones (named as 2-hydroxypyridine tautomers.

Mariella [Organic Syntheses, Collective Vol. IV, pp. 210-2, Rabjohn (1963)] describes a procedure for preparing 3-cyano-6-methyl-2(1H)-pyridinone by first reacting acetone with ethyl formate and sodium methoxide to produce sodium formylacetone and then heating it with cyanoacetamide in the presence of piperidine acetate.

Boatman et al [J. Org. Chem. 30, 3593-7 (1965)] show the reaction of 3-cyano-6-methyl-2(1H)-pyridinone with potassium amide in liquid ammonia and subsequent reaction of the resulting salt with methyl iodide to produce 3-cyano-6-ethyl-2(1H)-pyridinone (p. 3596, 3a).

Witzel [U.S. Pat. No. 3,654,291, issued Apr. 4, 1972] discloses as an intermediate in Example 13 the use of 3-cyano-6-methyl-2(1H)-pyridinone in the preparation of 3-acetyl-6-methyl-2(1H)-pyridinone, in turn used as an intermediate to prepare successively the corresponding 5-nitro and 5-amino derivatives.

Witzel [U.S. Pat. No. 3,754,088, issued Aug. 21, 1973] shows in Example 1 the use of 6-ethyl-4-methyl-2(1H)-pyridinone and 4,6-dimethyl-2(1H)-pyridinone as intermediates for preparing the corresponding 2-piperidinones.

Michel [U.S. Pat. No. 4,205,174, issued May 27, 1980] describes and claims the process for the production of 6-R-4-methyl-2(1H)-pyridinone, where R is, inter alia, a branched alkyl group or an unbranched alkyl group by reacting senecioic acid amide of the formula $(CH_3)_2C=C-CONH_2$ in a solvent at an elevated temperature in the presence of a Lewis acid, as catalyst, with an acyl chloride of the formula RCOCl, inserting the resulting reaction mixture into an aqueous phase whereby hydrolysis occurs, and separating the resulting 6-R-4-methyl-2(1H)-pyridinone by extraction through the buffering of the reaction mixture at a pH of 4 to 5. The product of Example 1 is 4,6-dimethyl-2(1H)-pyridinone.

Sakurai et al [Bull. Chem. Soc. Japan 40 (7), 1680-4 (1967) (Eng.)] show the preparation of 3-cyano-6-methyl-4-n-propyl-2(1H)-pyridinone (named as 2-hydroxypyridine tautomer) by refluxing a mixture of ethyl cyanoacetate, n—$C_3H_7$CH=CHCOCH$_3$, acetic acid and ammonium acetate in benzene.

Youngdale [U.S. Pat. No. 4,288,440, issued Sept. 8, 1981] shows 3-cyano-6-$R_1$-2(1H)-pyridinones as intermediates for preparing 3-$R_2$-6-$R_1$-2(1H)-pyridinones, antihyperglycemic agents, where $R_1$ is "alkyl of four to eight carbon atoms" and $R_2$ is tetrazolyl and carboxaldehyde.

Rogers et al [U.S. Pat. No. 3,926,935, issued Dec. 16, 1975] discloses and claims complexes of 4,4'-dinitrocarbanilide and 1-$R_1$-4-$R_3$-6-$R_4$-2(1H)-pyridinones where $R_1$ is methyl or ethyl, and $R_3$ and $R_4$ are each the same lower-alkyl, e.g., said complex of 1,4,6-trimethyl-2(1H)-pyridinone.

Johnson et al [U.S. Pat. No. 4,038,065, issued July 26, 1977] show 3-cyano-1-R-4-$R_1$-6-$R_2$-2(1H)-pyridinones, e.g., 3-cyano-1,4,6-trimethyl-2(1H)-pyridinone, as intermediates for preparing plant growth regulators and gametocidal agents.

SUMMARY OF THE INVENTION

A composition aspect of the invention resides in a cardiotonic composition for increasing cardiac contractility in a patient, said composition comprising a pharmaceutically acceptable carrier and, as the active ingredient thereof, a cardiotonically effective amount of 3-Q-4-R'-6-R-2(1H)-pyridinone, where Q is hydrogen or cyano, and R' is hydrogen, methyl, ethyl or n-propyl, and R is methyl, ethyl or n-propyl.

In a method aspect, the invention resides in a method for increasing cardiac contractility in a patient requiring such treatment which comprises the administration of a medicament comprising a pharmaceutically acceptable carrier and, as the active component thereof, a cardiotonically effective amount of 3-Q-4-R'-R-2(1H)-pyridinone, where Q, R' and R are defined as above.

DETAILED DESCRIPTION INCLUSIVE OF PREFERRED EMBODIMENTS

A composition aspect of the invention resides in a cardiotonic composition for increasing cardiac contractility, said composition comprising a pharmaceutically acceptable carrier and, as the active component thereof, a cardiotonically effective amount of 3-Q-4-R'-6-R-2(1H)-pyridinone having formula I

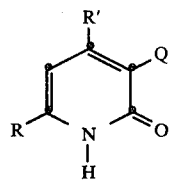

where Q is hydrogen or cyano, R' is hydrogen, methyl, ethyl or n-propyl, and R is methyl, ethyl or n-propyl. Preferred embodiments are said compounds of formula I where Q is cyano, R is methyl or ethyl and R' is hydrogen, methyl or ethyl.

A method aspect of the invention resides in the method for increasing cardiac contracility in a patient requiring such treatment which comprises administering orally or parenterally in a solid or liquid dosage form to such patient a cardiotonically effective amount of 3-Q-4-R'-6-R-2(1H)-pyridinone of formula I where Q is hydrogen or cyano, R' is hydrogen, methyl, ethyl or n-propyl, and R is methyl, ethyl or n-propyl. Preferred embodiments of this method aspect are those using as active component in the above-said composition embodiments said 2(1H)-pyridinone where Q is cyano, R is methyl or ethyl and R' is hydrogen, methyl or ethyl.

The manner of making and using the instant invention will now be generally described so as to enable a person skilled in the art of pharmaceutical chemistry to make and use the same.

The following examples will further illustrate the active ingredients of the cardiotonic composition and method aspects of the invention without, however, limiting it thereto. These active ingredients are generally known compounds and are prepared by known or generally known procedures as illustrated by a number of the references given hereinabove and specifically referred to hereinbelow.

1. 3-Cyano-6-methyl-2(1H)-pyridinone, was prepared according to Mariella (1963), supra.

2. 3-Cyano-6-ethyl-2(1H)-pyridinone, can be prepared according to Boatman et al., supra.

3. 3-Cyano-4,6-dimethyl-2(1H)-pyridinone, was prepared according to Basu (1930, p. 491) supra, and also was commercially available (Aldrich Chemical Co.).

4. 3-Cyano-4,6-diethyl-2(1H)-pyridinone, was prepared according to Basu (1930, p. 822) supra.

5. 3-Cyano-6-ethyl-4-methyl-2(1H)-pyridinone, can be prepared according to Bardhan, supra.

6. 3-Cyano-6-n-propyl-2(1H)-pyridinone, can be prepared according to Mariella (1951), supra.

7. 3-Cyano-6-methyl-4-n-propyl-2(1H)-pyridinone, can be prepared according to Sakurai, supra.

8. 3-Cyano-4,6-di-n-propyl-2(1H)-pyridinone was prepared as follows: A mixture containing 15.6 g of 4,6-nonanedione, 200 ml of methanol, 10 g of cyanoacetamide and 6 g of sodium methoxide was refluxed with stirring for 22 hours and then stripped to dryness in vacuo. The residue was dissolved in 100 ml of water and the solution acidified with acetic acid. The white precipitate was collected, washed with water, air-dried, recrystallized from isopropyl alcohol-n-hexane and dried in vacuo at 80°-85° C. to produce 16.7 g of 3-cyano-4,6-di-n-propyl-2(1H)-pyridinone, m.p. 151°-152° C.

9. 6-Methyl-2(1H)-pyridinone, was commercially available (Aldrich Chemical Co. No. 12,874-0).

10. 4,6-Dimethyl-2(1H)-pyridinone, was prepared by hydrolysis (and decarboxylation) of corresponding 3-cyano (and 3-carboxy) compound (Example 3 above).

11. 4,6-Diethyl-2(1H)-pyridinone, can be prepared according to Basu (1930, pp. 822-3), supra.

12. 6-Ethyl-4-methyl-2(1H)-pyridinone, can be prepared according to Bardhan, supra.

13. 6-n-Propyl-2(1H)-pyridinone, can be prepared according to Kochetkov, supra.

14. 6-Methyl-4-n-propyl-2(1H)-pyridinone, can be prepared according to procedure referred to in Example 11 by heating the corresponding 3-cyano compound of Example 7 with concentrated hydrochloric acid.

15. 6-Ethyl-2(1H)-pyridinone, can be prepared according to procedure referred to in Example 11 by heating the corresponding 3-cyano compound of Example 2 with concentrated hydrochloric acid.

16. 4,6-Di-n-propyl-2(1H)-pyridinone, can be prepared according to procedure referred to in Example 11 by heating the corresponding 3-cyano compound of Example 8 with concentrated hydrochloric acid.

The usefulness of the compounds of formula I as cardiotonic agents is demonstrated by their effectiveness in standard pharmacological test procedures, for example, in causing a significant increase in contractile force of the isolated cat or guinea pig atria and papillary muscle and/or in causing a significant increase in the cardiac contractile force in the anesthetized dog with lower or minimal changes in heart rate and blood pressure. Detailed descriptions of these test procedures appear in U.S. Pat. No. 4,072,746, issued Feb. 7, 1980.

When tested by said isolated cat or guinea pig atria and papillary muscle procedure, the compounds of formula I at doses of 10, 30 and/or 100 µg/ml., were found to cause significant increases, that is, greater than 25% (cat) or 30% (g.pig) in papillary muscle force and significant increases, that is, greater than 25% (cat) or 30% (g.pig) in right atrial force, while causing a lower percentage increase (about one-half or less than the percentage increase in right atrial force or papillary muscle force) in right atrial rate. Because of the lower control active tensions of guinea pig tissues, the percent change from control values of both rate and force responses is elevated slightly, i.e., 5%. Thus, whereas cardiotonic activity is ascertained with a papillary muscle force or right atrial force increase of 26% and greater in the cat test, corresponding activity in the guinea pig test is designated with a papillary muscle force or right atrial force increase of 31% or greater. For example, when tested by said cat atria and papillary muscle procedure, the following illustrative compounds were found to cause respective papillary muscle force and right atrial force increases as follows: the compound of Example 9, 41% and 30% at 100 µg/ml; and, the compound of Example 10, 60% and 33% at 100 µg/ml. When tested by said guinea pig atria and papillary muscle procedure, the following illustrative compounds were found to cause papillary muscle force and right atrial force increases as follows: the compound of Example 3, 32% and 33% at 10 µg/ml, 68% and 45% at 30 µg/ml and 117% and 104% at 100 μg/ml; the compound of Example 1, 89% and 82% at 100 μg/ml; the compound of Example 4, 118% and 274% at 100 μg/ml; and, the compound of Example 8, 72% and 322% at 100 μg/ml.

When tested by said anesthetized dog procedure, the compounds of formula I at doses of 1.0, 3.0 and/or 10.0 mg/kg administered intravenously were found to cause significant increases, that is, 25% or greater, in cardiac contractile force or cardiac contractility with lower changes in heart rate and blood pressure. For example, when tested by this procedure, the compound of Example 1 was found to cause increases of 35, 61 and 128% at respective doses of 1.0, 3.0 and 10.0 mg/kg.

The present invention thus comprehends within its scope a cardiotonic composition for increasing cardiac contractility, said composition comprising in unit dosage form a pharmaceutically acceptable carrier and, as the active component thereof, the compound of formula I. The invention also comprehends within its scope the method for increasing cardiac contractility in a patient requiring such treatment which comprises administering to such patient a cardiotonically effective amount of the compound of formula I. In clinical practice said compound will normally be administered orally or parenterally in a wide variety of dosage forms.

Solid compositions for oral administration include compressed tablets, pills, powders and granules. In such solid compositions, at least one of the active compounds is admixed with at least one inert diluent such as starch, calcium carbonate, sucrose or lactose. These compositions may also contain additional substances other than inert diluents, e.g., lubricating agents, such as magnesium stearate, talc, and the like.

Liquid compositions for oral administration include pharmaceutically acceptable emulsions, solutions, suspensions, syrups and elixirs containing inert diluents commonly used in the art, such as water and liquid paraffin. Besides inert diluents such compositions may also contain adjuvants, such as wetting and suspending agents, and sweetening, flavoring, perfuming and preserving agents. According to the invention, the compounds for oral administration also include capsules of absorbable material, such as gelatin, containing said active component with or without the addition of diluents or excipients.

Preparations according to the invention for parenteral administration include sterile aqueous, aqueous-organic, and organic solutions, suspensions and emulsions. Examples of organic solvents or suspending media are propylene glycol, polyethylene glycol, vegetable oils such as olive oil and injectable organic ester such as ethyl oleate. These compositions can also contain adjuvants such as stabilizing, preserving, wetting, emulsifying and dispersing agents.

They can be sterilized, for example by filtration through a bacterial-retaining filter, by incorporation of sterilizing agents in the compositions, by irradiation or by heating. They can also be manufactured in the form of sterile solid compositions which can be dissolved in sterile water or some other sterile injectable medium immediately before use.

The percentage of active component in the said composition and method for increasing cardiac contractility can be varied to that a suitable dosage is obtained. The dosage administered to a particular patient is variable, depending upon the clinician's judgement using as the criteria: the route of administration, the duration of treatment, the size and condition of the patient, the potency of the active component and the patient's response thereto. An effective dosage amount of active component can thus only be determined by the clinician considering all criteria and utilizing his best judgement on the patient's behalf.

We claim:

1. A cardiotonic composition for increasing cardiac contractility, said composition comprising a pharmaceutically acceptable inert carrier and, as the active component thereof, a cardiotonically effective amount of 3-Q-4-R'-6-R-2(1H)pyridinone having the formula

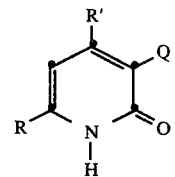

where Q is hydrogen or cyano, R' is hydrogen, methyl, ethyl or n-propyl, and R is methyl, ethyl or n-propyl.

2. A composition according to claim 1 where Q is cyano, R is methyl or ethyl and R' is hydrogen, methyl or ethyl.

3. A composition according to claim 1 where the active component is 3-cyano-6-methyl-2(1H)-pyridinone.

4. A composition according to claim 1 where the active component is 3-cyano-4,6-dimethyl-2(1H)-pyridinone.

5. A composition according to claim 1 where the active component is 3-cyano-4,6-diethyl-2(1H)-pyridinone.

6. The method for increasing cardiac contractility in a patient requiring such treatment which comprises administering orally or parenterally in a solid or liquid dosage form to said patient a cardiotonically effective amount of 3-Q-4-R'-6-R-2(1H)-pyridinone having the formula

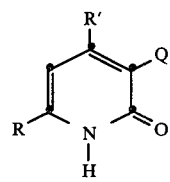

where Q is hydrogen or cyano, R' is hydrogen, methyl, ethyl or n-propyl, and R is methyl, ethyl or n-propyl.

7. A method according to claim 6 using the 2(1H)-pyridinone where Q is cyano, R is methyl or ethyl and R' is hydrogen, methyl or ethyl.

8. A method according to claim 6 using 3-cyano-6-methyl-2(1H)-pyridinone.

9. A method according to claim 6 using 3-cyano-4,6-dimethyl-2(1H)-pyridinone.

10. A method according to claim 6 using 3-cyano-4,6-diethyl-2(1H)-pyridinone.

* * * * *